US011813047B2

(12) United States Patent
Meyer et al.

(10) Patent No.: US 11,813,047 B2
(45) Date of Patent: *Nov. 14, 2023

(54) AUTOMATIC QUANTIFICATION OF CARDIAC MRI FOR HYPERTROPHIC CARDIOMYOPATHY

(71) Applicant: University of Virginia Patent Foundation, Charlottesville, VA (US)

(72) Inventors: Craig H. Meyer, Charlottesville, VA (US); Anudeep Konda, Los Angeles, CA (US); Christopher M. Kramer, Charlottesville, VA (US); Xue Feng, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 160 days.

This patent is subject to a terminal disclaimer.

(21) Appl. No.: 17/335,518

(22) Filed: Jun. 1, 2021

(65) Prior Publication Data
US 2021/0287367 A1 Sep. 16, 2021

Related U.S. Application Data

(63) Continuation of application No. 16/295,939, filed on Mar. 7, 2019, now Pat. No. 11,024,025.
(Continued)

(51) Int. Cl.
G06T 7/00 (2017.01)
G06T 7/62 (2017.01)
(Continued)

(52) U.S. Cl.
CPC ............ *A61B 5/0263* (2013.01); *A61B 5/029* (2013.01); *A61B 5/1071* (2013.01);
(Continued)

(58) Field of Classification Search
CPC .................... G06T 7/0012; G06T 7/11; G06T 2207/20084; G06T 2207/10116;
(Continued)

(56) References Cited

U.S. PATENT DOCUMENTS 7,583,082 B1 9/2009 Hu et al.
7,642,777 B1 1/2010 Meyer et al.
(Continued)

FOREIGN PATENT DOCUMENTS

WO 2010062557 6/2010
WO 2012145547 10/2012
(Continued)

OTHER PUBLICATIONS

Avendi MR, Kheradvar A, Jafarkhani H. A combined deep-learning and deformable-model approach to fully automatic segmentation of the left ventricle in cardiac MRI. Med Image Anal.2016;30:108-119.
(Continued)

*Primary Examiner* — Santiago Garcia
(74) *Attorney, Agent, or Firm* — Meunier Carlin & Curfman LLC

(57) ABSTRACT

In one aspect the disclosed technology relates to embodiments of a method which, includes acquiring magnetic resonance imaging data, for a plurality of images, of the heart of a subject. The method also includes segmenting, using cascaded convolutional neural networks (CNN), respective portions of the images corresponding to respective epicardium layers and endocardium layers for a left ventricle (LV) and a right ventricle (RV) of the heart. The segmenting is used for extracting biomarker data from segmented portions of the images and, in one embodiment, assessing hypertrophic cardiomyopathy from the biomarker
(Continued)

data. The method further includes segmenting processes for T1 MRI data and LGE MRI data.

22 Claims, 9 Drawing Sheets

Related U.S. Application Data

(60) Provisional application No. 62/801,253, filed on Feb. 5, 2019, provisional application No. 62/639,640, filed on Mar. 7, 2018.

(51) Int. Cl.

| | |
|---|---|
| *G06T 7/13* | (2017.01) |
| *G06T 7/70* | (2017.01) |
| *G06K 9/62* | (2022.01) |
| *A61B 5/029* | (2006.01) |
| *A61B 5/026* | (2006.01) |
| *A61B 5/00* | (2006.01) |
| *A61B 5/107* | (2006.01) |
| *G06T 7/11* | (2017.01) |
| *G06F 18/211* | (2023.01) |
| *G06V 10/764* | (2022.01) |
| *G06V 10/82* | (2022.01) |

(52) U.S. Cl.
CPC .......... *A61B 5/1075* (2013.01); *A61B 5/7267* (2013.01); *G06F 18/211* (2023.01); *G06T 7/0012* (2013.01); *G06T 7/11* (2017.01); *G06T 7/13* (2017.01); *G06T 7/62* (2017.01); *G06T 7/70* (2017.01); *G06V 10/764* (2022.01); *G06V 10/82* (2022.01); *G06T 2207/10088* (2013.01); *G06T 2207/20084* (2013.01); *G06T 2207/30048* (2013.01); *G06V 2201/031* (2022.01)

(58) Field of Classification Search
CPC ....... G06T 2207/30004; G06T 2200/04; G06T 7/70; G06T 2207/30048; G06T 2207/10088; G06T 2210/41; G06T 2207/30024; G06T 2207/20156; G06T 7/20; G06T 7/73; G16H 30/20; G16H 30/40; A61B 2576/00; A61B 5/0013; A61B 2576/023; A61B 6/503; A61B 2034/105; A61B 5/1075; A61B 5/7267; A61B 5/021; A61B 5/7264; A61B 5/0044; A61B 8/00; G06F 19/321; Y10S 128/922; G06K 9/6212; G06K 9/6223; G06N 3/08; G06N 20/00; G06N 3/02; A61M 2021/005; G01R 33/12

See application file for complete search history.

(56) References Cited

U.S. PATENT DOCUMENTS

| | | |
|---|---|---|
| 7,888,935 B1 | 2/2011 | Tan et al. |
| 8,026,720 B1 | 9/2011 | Chen et al. |
| 8,094,907 B1 | 1/2012 | Meyer et al. |
| 8,238,634 B1 | 8/2012 | Meyer et al. |
| 8,306,289 B1 | 11/2012 | Meyer et al. |
| 8,440,167 B2 | 5/2013 | Beller et al. |
| 8,700,127 B2 | 4/2014 | Salerno et al. |
| 8,737,709 B2 * | 5/2014 | Kamath ................. G16H 50/20 382/128 |
| 9,183,626 B2 | 11/2015 | Zhao et al. |
| 9,322,896 B2 | 4/2016 | Fielden et al. |
| 9,589,345 B2 | 3/2017 | Zhao et al. |
| 9,651,645 B2 | 5/2017 | Fielden et al. |
| 9,761,806 B1 * | 9/2017 | Han ..................... H01L 51/0048 |
| 9,811,924 B2 | 11/2017 | Johnson et al. |
| 9,874,623 B2 | 1/2018 | Fielden et al. |
| 9,910,118 B2 | 3/2018 | Feng et al. |
| 9,953,439 B2 | 4/2018 | Salerno et al. |
| 9,989,611 B2 | 6/2018 | Zhao et al. |
| 10,143,384 B2 | 12/2018 | Chen et al. |
| 11,478,226 B2 * | 10/2022 | Kezurer ................. G16H 50/30 |
| 2006/0027744 A1 * | 2/2006 | Stults ..................... H01J 49/165 250/288 |
| 2007/0116339 A1 * | 5/2007 | Shen ......................... G06T 7/12 382/128 |
| 2008/0317319 A1 * | 12/2008 | Lautenschlager ...... A61B 90/36 382/131 |
| 2010/0201687 A1 * | 8/2010 | Breeuwer ............... G06T 15/08 345/424 |
| 2011/0143947 A1 * | 6/2011 | Chamberlin ....... G01N 21/6452 506/7 |
| 2012/0027276 A1 * | 2/2012 | Chono .................. A61B 8/5223 382/128 |
| 2013/0004040 A1 * | 1/2013 | Chen ..................... G06T 11/005 382/131 |
| 2014/0364723 A1 | 12/2014 | Meyer et al. |
| 2015/0282719 A1 | 10/2015 | Fielden et al. |
| 2015/0282733 A1 | 10/2015 | Fielden et al. |
| 2015/0287222 A1 | 10/2015 | Zhao et al. |
| 2017/0035319 A1 | 2/2017 | Zhao et al. |
| 2017/0109881 A1 * | 4/2017 | Avendi .................. G06T 3/0006 |
| 2017/0202478 A1 | 7/2017 | Handsfield et al. |
| 2017/0261584 A1 * | 9/2017 | James ................ G01R 33/4835 |
| 2017/0307705 A1 | 10/2017 | Mugler, III et al. |
| 2017/0328972 A1 | 11/2017 | Fielden et al. |
| 2017/0337682 A1 * | 11/2017 | Liao ............................ G06T 7/30 |
| 2018/0137244 A1 * | 5/2018 | Sorenson ............... G16H 50/70 |
| 2018/0218502 A1 * | 8/2018 | Golden ..................... G06T 7/11 |
| 2018/0259608 A1 * | 9/2018 | Golden ............ G01R 33/56308 |
| 2018/0292499 A1 | 10/2018 | Meyer et al. |
| 2019/0122074 A1 * | 4/2019 | Zhang ..................... G06N 3/0454 |
| 2019/0128989 A1 * | 5/2019 | Braun ..................... G06N 3/084 |
| 2019/0147215 A1 * | 5/2019 | Al-Kofahi ............... G06T 7/194 382/133 |
| 2019/0150764 A1 * | 5/2019 | Arnold .................... A61B 5/055 |
| 2019/0244348 A1 * | 8/2019 | Buckler .................... G06T 7/11 |
| 2020/0027237 A1 * | 1/2020 | Baumgartner ........ G06T 11/001 |
| 2020/0085382 A1 * | 3/2020 | Taerum .................. A61B 5/055 |
| 2020/0380675 A1 * | 12/2020 | Golden ................. G06V 10/82 |

FOREIGN PATENT DOCUMENTS

| | | |
|---|---|---|
| WO | 2013023214 | 2/2013 |
| WO | 2016004423 | 1/2016 |

OTHER PUBLICATIONS

Avendi MR, Kheradvar A, Jafarkhani H. Automatic segmentation of the right ventricle from cardiac MRI using a learning-based approach. Magn Reson Med. 2017;78(6):2439-2448.

Billet F, Sermesant M, Delingette H, Ayache N. Cardiac motion recovery and boundary conditions estimation by coupling an electromechanical model and cine-MRI data. In: International Conference on Functional Imaging and Modeling of the Heart; 2009:376-385.

Bui TD, Shin J, Moon T. 3d densely convolution networks for volumetric segmentation. arXiv Prepr arXiv170903199. 2017.

Çiçek, Ö., Abdulkadir, A., Lienkamp, S.S., Brox, T. and Ronneberger, O., Oct. 2016. 3D U-Net: learning dense volumetric segmentation from sparse annotation. In International Conference on Medical Image Computing and Computer-Assisted Intervention (pp. 424-432). Springer International Publishing.

Cobzas D, Schmidt M. Increased discrimination in level set methods with embedded conditional random fields. In: Computer Vision and Pattern Recognition, 2009. CVPR 2009. IEEE Conference 2009:328-335.

Cocosco CA, Niessen WJ, Netsch T, et al. Automatic image-driven segmentation of the ventricles in cardiac cine MRI. J Magn Reson Imaging. 2008;28(2):366-374.

(56) References Cited

OTHER PUBLICATIONS

Cordero-Grande L, Vegas-Sánchez-Ferrero G, Casaseca-de-la-Higuera P, et al. Unsupervised 4D myocardium segmentation with a Markov Random Field based deformable model. Med Image Anal. 2011;15(3):283-301.

Dreijer JF, Herbst BM, Du Preez JA. Left ventricular segmentation from MRI datasets with edge modelling conditional random fields. BMC Med Imaging. 2013;13(1):24.

Geremia E, Clatz O, Menze BH, Konukoglu E, Criminisi A, Ayache N. Spatial decision forests for MS lesion segmentation in multi-channel magnetic resonance images. Neuroimage. 2011;57(2):378-390.

Huang S, Liu J, Lee LC, et al. An image-based comprehensive approach for automatic segmentation of left ventricle from cardiac short axis cine mr images. J Digit Imaging. 2011;24(4):598-608.

Jolly M. Fully automatic left ventricle segmentation in cardiac cine MR images using registration and minimum surfaces. MIDAS Journal-Cardiac MR Left Vent Segmentation Chall. 2009; 4:59.

Kedenburg G, Cocosco CA, Köthe U, Niessen WJ, Vonken EPA, Viergever MA. Automatic cardiac MRI myocardium segmentation using graphcut. In: Medical Imaging 2006: Image Processing. vol. 6144, 2006:61440A.

Kramer, C.M., Appelbaum, E., Desai, M.Y., Desvigne-Nickens, P., DiMarco, J.P., Friedrich, M.G., Geller, N., Heckler, S., Ho, C.Y., Jerosch-Herold, M. and Ivey, E.A., 2015. Hypertrophic Cardiomyopathy Registry: The rationale and design of an international, observational study of hypertrophic cardiomyopathy. American heart journal, 170(2), pp. 223-230.

Lempitsky V, Verhoek M, Noble JA, Blake A. Random forest classification for automatic delineation of myocardium in real-time 3D echocardiography. In: International Conference on Functional Imaging and Modeling of the Heart. ; 2009:447-456.

Margeta J, Geremia E, Criminisi A, Ayache N. Layered spatio-temporal forests for left ventricle segmentation from 4D cardiac MRI data. In: International Workshop on Statistical Atlases and Computational Models of the Heart; 2011:109-119.

Ngo TA, Carneiro G. Fully Automated Non-rigid Segmentation with Distance Regularized Level Set Evolution Initialized and Constrained by Deep-Structured Inference. In: CVPR. ; 2014:3118-3125.

Petitjean C, Dacher J-N. A review of segmentation methods in short axis cardiac MR images. Med Image Anal. 2011;15(2):169-184.

Pluempitiwiriyawej C, Moura JMF, Wu Y-JL, Ho C. STACS: New active contour scheme for cardiac MR image segmentation. IEEE Trans Med Imaging. 2005;24(5):593-603.

Suinesiaputra A, Bluemke DA, Cowan BR, et al. Quantification of LV function and mass by cardiovascular magnetic resonance: multi-center variability and consensus contours. J Cardiovasc Magn Reson. 2015;17(1):63.

Suinesiaputra, Avan, et al. "Fully-automated left ventricular mass and volume MRI analysis in the UK Biobank population cohort: evaluation of initial results." The international journal of cardiovascular imaging 34.2 (2018): 281-291.

Tran PV. A fully convolutional neural network for cardiac segmentation in short-axis MRI. arXiv Prepr arXiv160400494. 2016.

Van Assen HC, Danilouchkine MG, Frangi AF, et al. SPASM: a 3D-ASM for segmentation of sparse and arbitrarily oriented cardiac MRI data. Med Image Anal. 2006;10(2):286-303.

Yang XL, Gobeawan L, Yeo SY, Tang WT, Wu ZZ, Su Y. Automatic segmentation of left ventricular myocardium by deep convolutional and de-convolutional neural networks. In: Computing in Cardiology Conference (CinC), 2016; 2016:81-84.

Yu F, Koltun V. Multi-scale context aggregation by dilated convolutions. arXiv Prepr arXiv151107122. 2015.

Zhang H, Wahle A, Johnson RK, Scholz TD, Sonka M. 4-D cardiac MR image analysis: left and right ventricular morphology and function. IEEE Trans Med Imaging. 2010;29(2):350-364.

Zhuang X, Hawkes DJ, Crum WR, et al. Robust registration between cardiac MRI images and atlas for segmentation propagation. In: Medical Imaging 2008: Image Processing. vol. 6914;2008:691408.

\* cited by examiner (a)

(b)

(c)

AUTOMATIC QUANTIFICATION OF CARDIAC MRI FOR HYPERTROPHIC CARDIOMYOPATHY

CROSS REFERENCE TO RELATED APPLICATIONS

This application claims priority to and incorporates entirely by reference corresponding U.S. Provisional Patent Application Ser. No. 62/639,640 filed on Mar. 7, 2018, and U.S. Provisional Patent Application Ser. No. 62/801,253 filed on Feb. 5, 2019, both entitled "Automatic Quantification of Cardiac MRI for Hypertrophic Cardiomyopathy with GPU."

STATEMENT REGARDING FEDERALLY SPONSORED RESEARCH

This invention was made with government support under Grant No. HL117006, awarded by The National Institutes of Health. The government has certain rights in the invention.

FIELD

This disclosure relates to magnetic resonance imaging operations that utilize convolutional neural networks to segment image data related to a heart of a subject.

BACKGROUND

Hypertrophic cardiomyopathy (HCM) is the most common monogenic heart disease. It is characterized by unexplained left ventricular hypertrophy, myofibrillar disarray and myocardial fibrosis. While the majority of patients with HCM are asymptomatic, serious consequences are experienced in a subset of affected individuals who may present initially with sudden cardiac death or heart failure.

Generally, HCM is a cardiovascular disease that affects the heart muscle, also known as the myocardium. It causes thickening of the heart muscle, especially in the ventricles (or lower heart chambers). Thickening of the myocardium occurs most commonly at the septum, which is the muscular wall that separates the left and right side of the heart. The thickened septum may cause a narrowing that can block or reduce the blood flow from the left ventricle to the aorta—a condition called "outflow tract obstruction." The ventricles must pump harder to overcome the narrowing or blockage. HCM also may cause thickening in other parts of the heart muscle, such as the bottom of the heart called the apex, right ventricle, or throughout the entire left ventricle. The degree and location of thickening is fairly random. Myocardial thickening also causes cellular changes which leads to stiffening of the tissue. This restricts the normal relaxation of the ventricle, disabling it from fully filling with blood. Since there is less blood at the end of filling, there is less oxygen-rich blood pumped to the organs and muscles, which leads to ischemia.

Currently known clinical risk markers are only modestly effective at identifying those at highest risk. Currently the segmentation is performed manually by experienced cardiologists due to the lack of robust automatic methods. As the number of cardiac magnetic resonance (CMR) images is very large (150-200 per patient), the process is very time-consuming. The segmentations from a multi-person, multi-site study suffer from a significant inter-observer variability as people differ in their expertise and notion of the correct segmentation. Usually, only the end-systole and end-diastole phases of the cardiac cycle undergo segmentation as they reveal most of the information, and it would take a painfully long amount of time for humans to segment all the cardiac phases. This means that the bio-marker quantification is done solely based on static information and no details corresponding to the motion of myocardium, which are of much significance, are considered.

Segmentation of magnetic resonance imaging (MRI) for HCM patients is particularly challenging as they have much higher variability in shape and size of the heart chambers. This is because the amount and place of thickening of the myocardium is totally random. It would be very difficult for a generic method to achieve good results. Some approaches that perform both LV and RV segmentations treat them as two separate problems, thus ignoring their relative positions and shapes. Avendi et al. [21] also proposed a technique to segment the RV. A dice score of 0.81 was reported on the endocardium. Tran et al. [20] also suggested their LV segmentation approach can be used, without any changes, to segment the RV. Furthermore, none of these studies focus on HCM populations, and a model trained on normal and other patient populations is very likely to perform poorly on an HCM dataset due to the notable differences in contrast and shape.

A need continues to exist in the art of magnetic resonance imaging for a robust automatic segmentation method could greatly reduce the cost and improve the quality of CMR marker quantification. Moreover, an efficient automatic segmentation method can be viewed as one segmenter, which reduces the inter-observer variability. Also, a segmenting method and system disclosed herein can easily perform segmentation on all cardiac phases in a very short time, which is almost impossible for a human. This will allow diagnosticians, for the first time, to study the cardiac wall motion that could reveal interesting details pertaining to the differences in an HCM heart, in comparison with normal heart, that could potentially be a remarkable bio-marker.

SUMMARY

In one aspect the disclosed technology relates to embodiments of a method which includes acquiring magnetic resonance imaging data, for a plurality of images, of the heart of a subject. The method also includes segmenting, using cascaded convolutional neural networks (CNN), respective portions of the images corresponding to respective epicardium layers and endocardium layers for a left ventricle (LV) and a right ventricle (RV) of the heart. The segmenting is used for extracting biomarker data from segmented portions of the images and, in one embodiment, assessing hypertrophic cardiomyopathy from the biomarker data.

In another aspect the method includes acquiring magnetic resonance imaging data, for a plurality of images, of the heart of a subject. The method includes using a first set of cascaded convolutional neural networks (CNN) operating with cine image data sets to segment respective portions of the plurality of images corresponding to respective epicardium layers and endocardium layers for a left ventricle (LV) and a right ventricle (RV) of the heart. A second set of cascaded convolutional neural networks (CNN) operate on T1 image data sets to segment additional images corresponding to the respective epicardium layer and endocardium layer for the LV of the heart. The method includes extracting biomarker data from segmented portions of the cine image data sets and the T1 image data sets and assessing hypertrophic cardiomyopathy from the biomarker data.

In another embodiment, the disclosed technology encompasses a system having at least one processor and at least one memory device coupled to the processor for storing computer-readable instructions which, when executed by the at least one processor, cause the system to perform functions of a method. The system implements a method of acquiring magnetic resonance imaging data, for a plurality of images, of a heart of a subject, segmenting, using cascaded convolutional neural networks (CNN), respective portions of the images corresponding to respective epicardium layers and endocardium layers for a left ventricle (LV) and a right ventricle (RV) of the heart, and extracting biomarker data from segmented portions of the images. The method further includes assessing hypertrophic cardiomyopathy from the biomarker data.

In another embodiment of this disclosure, a non-transitory computer-readable medium has stored instructions that, when executed by one or more processors, cause a computing device to perform functions of a method. The method includes acquiring magnetic resonance imaging data, for a plurality of images, of a heart of a subject, segmenting, using cascaded convolutional neural networks (CNN), respective portions of the images corresponding to respective epicardium layers and endocardium layers for a left ventricle (LV) and a right ventricle (RV) of the heart; extracting biomarker data from segmented portions of the images, and assessing hypertrophic cardiomyopathy from the biomarker data.

Other aspects and features according to the example embodiments of the disclosed technology will become apparent to those of ordinary skill in the art, upon reviewing the following detailed description in conjunction with the accompanying figures.

DETAILED DESCRIPTION

Figure 1:
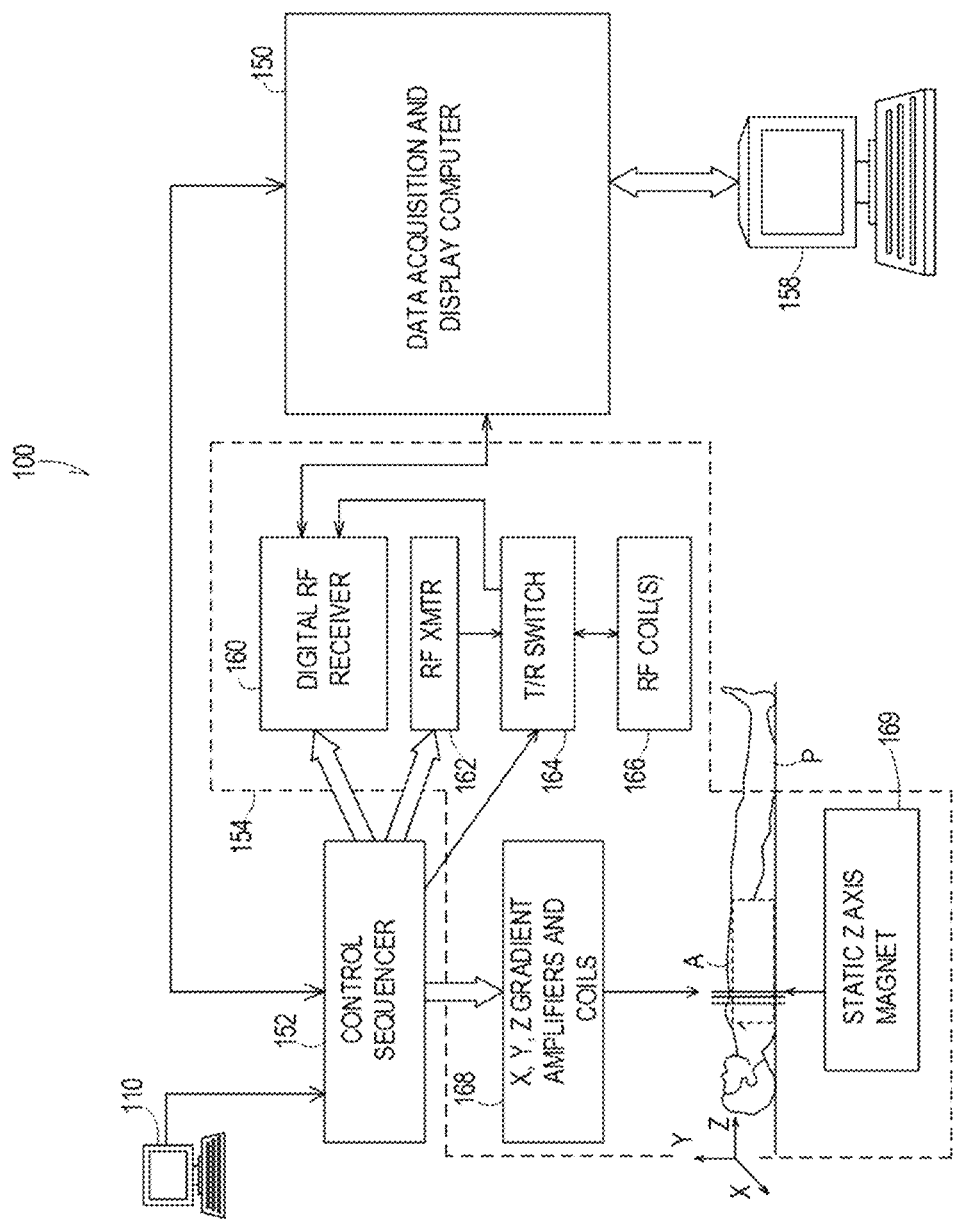
FIG. 1 is a system diagram illustrating an operating environment capable of implementing aspects of the disclosed technology.

In some aspects, the disclosed technology relates to free-breathing parameter mapping with high-contrast image registration. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the nth reference in the list. For example, [5] refers to the 5th reference in the list, namely Huang S, Liu J, Lee L C, et al. An image-based comprehensive approach for automatic segmentation of left ventricle from cardiac short axis cine mr images. *J Digit Imaging.* 2011; 24(4):598-608. All references cited and discussed in this specification are incorporated herein by reference in their entireties and to the same extent as if each reference was individually incorporated by reference.

Generally, embodiments of the present disclosure provide, among other things, an automatic quantification of cardiac MRI (and related method and computer readable media) for hypertrophic cardiomyopathy (HCM), and, optionally, with graphics processing units (GPU). In accordance with the quantification of HCM for diagnostic purposes, the embodiments shown herein are generally directed, without limitation to developing a fully automatic cascaded deep learning model to accurately segment both epicardium and endocardium of left ventricles (LV) and right ventricles (RV) from cine images. The automation includes developing deep learning models to accurately segment the epicardium and endocardium of LV from T1 images. Without limiting the disclosure to any particular embodiments, the segmenting protocols of this disclosure allow for quantifying at least biomarkers including, but not limited to, LV wall thickness, LV mass, RV mass, LV ejection fraction, RV ejection fraction, and mean myocardial T1.

A detailed description of aspects of the disclosed technology, in accordance with various example embodiments, will now be provided with reference to the accompanying drawings. The drawings form a part hereof and show, by way of illustration, specific embodiments and examples. In referring to the drawings, like numerals represent like elements throughout the several figures.

FIG. 1 is a system diagram illustrating an operating environment capable of implementing aspects of the disclosed technology in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a subject P to be imaged, for example, to implement magnetic resonance imaging sequences in accordance with various example embodiments of the disclosed technology described herein. An image of an area of interest A of the subject P (which may also be referred to herein as a "region of interest") may be shown on display 158. The display 158 may be implemented through a variety of output interfaces, including a monitor, printer, or data storage.

The area of interest A corresponds to a region associated with one or more physiological activities in subject P. The area of interest shown in the example embodiment of FIG. 1 corresponds to a chest region of subject P, but it should be appreciated that the area of interest for purposes of implementing various aspects of the disclosure presented herein is not limited to the chest area. It should be recognized and appreciated that the area of interest in various embodiments may encompass various areas of subject P associated with various physiological characteristics, such as, but not limited to the heart region. Physiological activities that may be evaluated by methods and systems in accordance with various embodiments of the disclosed technology may include, but are not limited to cardiac activity and conditions.

It should be appreciated that any number and type of computer-based medical imaging systems or components, including various types of commercially available medical imaging systems and components, may be used to practice certain aspects of the disclosed technology. Systems as described herein with respect to example embodiments are not intended to be specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the disclosed technology may include any device configured to acquire, collect, or otherwise obtain data, or to receive data from a data acquisition device within the system, an independent data acquisition device located on-site or off-site, or another data collection, storage, or processing device.

Figure 2:
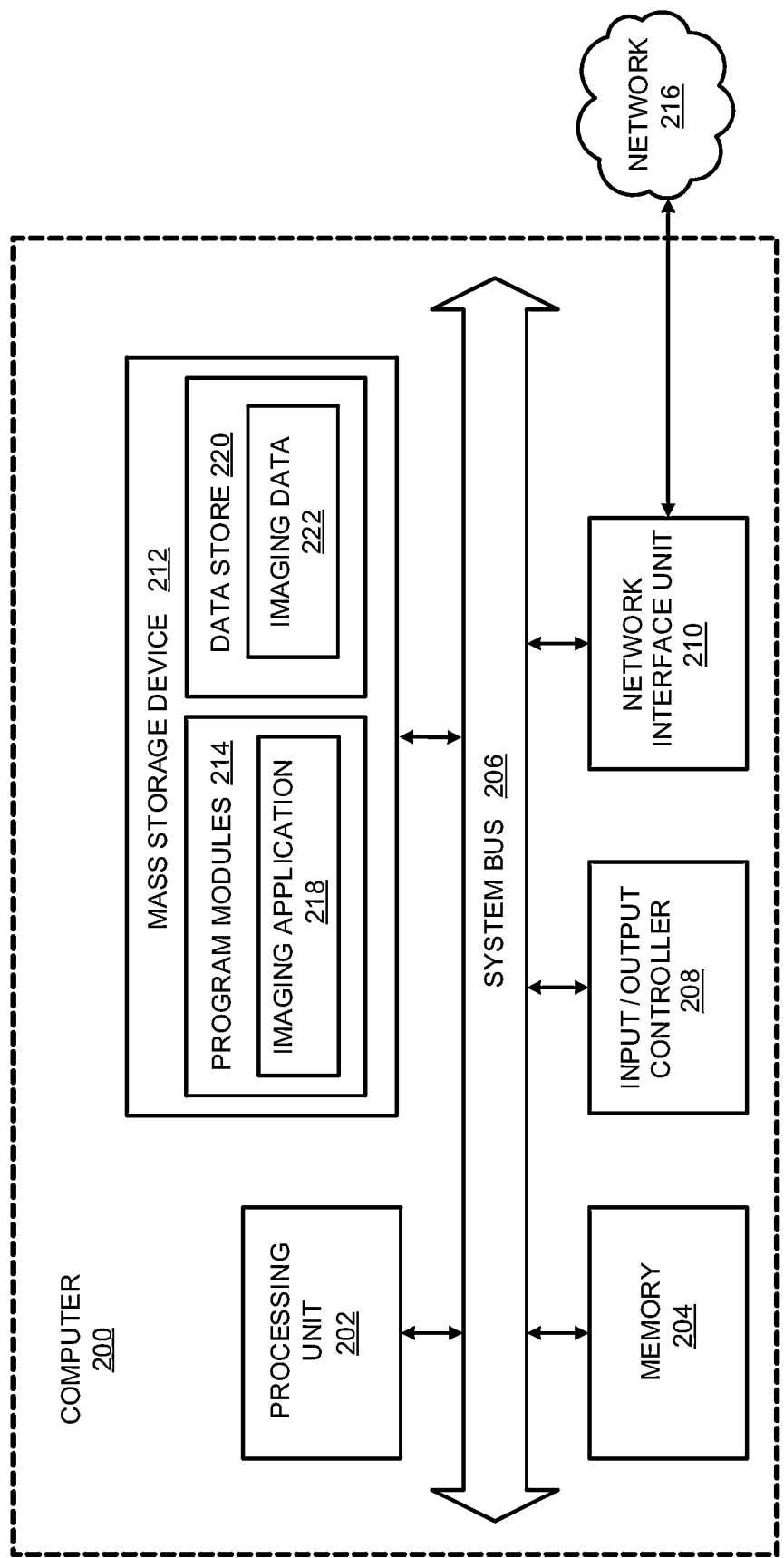
FIG. 2 is a computer architecture diagram showing a general computing system capable of implementing aspects of the disclosed technology.

FIG. 2 is a computer architecture diagram showing a general computing system capable of implementing aspects of the disclosed technology in accordance with one or more embodiments described herein. A computer 200 may be configured to perform one or more functions associated with embodiments illustrated in one or more of FIGS. 3-12. For example, the computer 200 may be configured to perform various aspects of free-breathing parameter mapping with high-contrast image registration in accordance with example embodiments, such as magnetic resonance imaging data acquisition, image registration, and calculating parameter maps. It should be appreciated that the computer 200 may be implemented within a single computing device or a computing system formed with multiple connected computing devices. The computer 200 may be configured to perform various distributed computing tasks, in which processing and/or storage resources may be distributed among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of FIGS. 3-12 discussed below. The program modules 214 may include an imaging application 218 for performing data acquisition and/or processing functions as described herein, for example to acquire and/or process image data corresponding to magnetic resonance imaging of an area of interest. The computer 200 can include a data store 220 for storing data that may include imaging-related data 222 such as acquired data from the implementation of magnetic resonance imaging in accordance with various embodiments of the disclosed technology.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. "Computer storage media", "computer-readable storage medium" or "computer-readable storage media" as described herein do not include transitory signals.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology.

The computer storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with one or more example embodiments and implementations illustrated in FIGS. 3-12. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202. Encoding the program modules 214 may also transform the physical structure of the computer-storage media. The specific transformation of physical structure may depend on various factors, in different implementations of this description. Examples of such factors may include, but are not limited to, the technology used to implement the computer-storage media, whether the computer storage media are characterized as primary or secondary storage, and the like. For example, if the computer storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Example Implementations and Results

Various aspects of the disclosed technology may be still more fully understood from the following description of example implementations and corresponding results and the images of FIGS. 3-12. Some experimental data are presented herein for purposes of illustration and should not be construed as limiting the scope of the disclosed technology in any way or excluding any alternative or additional embodiments.

Figure 3:
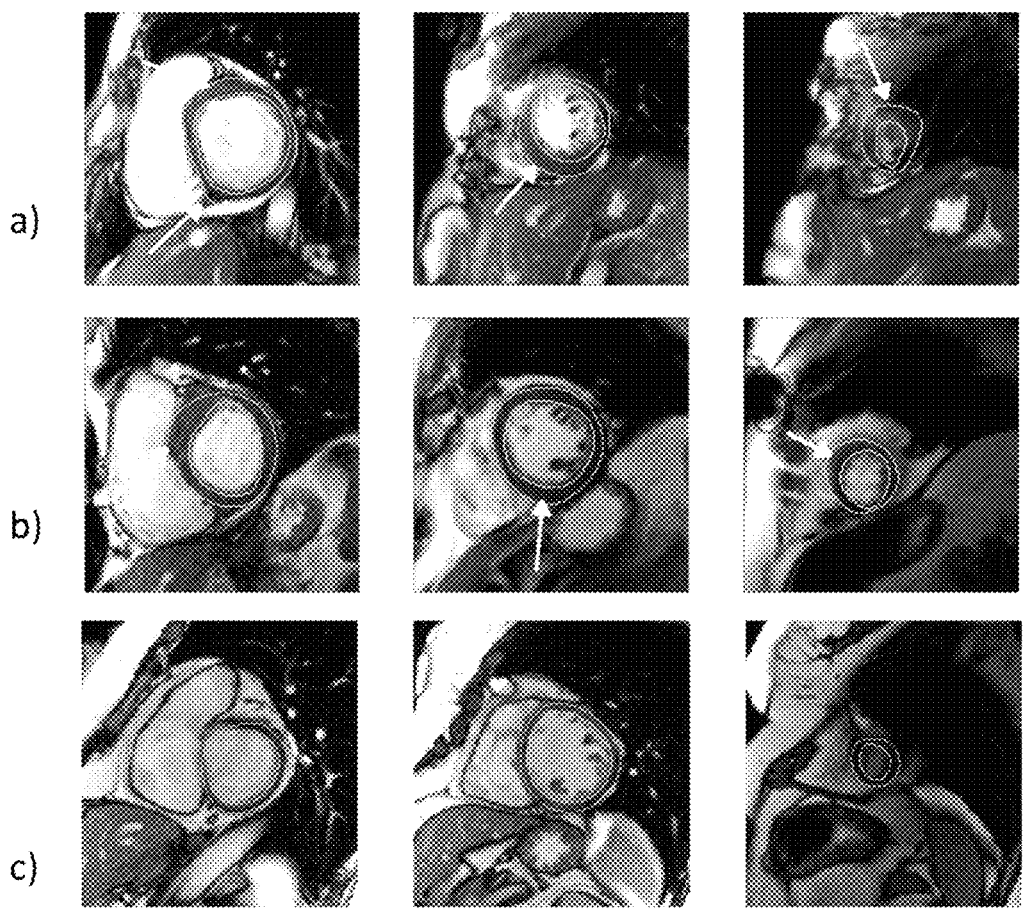
FIG. 3 illustrates a comparison of HCM (a, b) with a normal heart (c) and incorporates arrows pointing to the hypertrophy in myocardium as diagnosed with the technology described herein.

There are several challenges in automating the heart chamber segmentation task, namely, the heterogeneities in the brightness of LV cavity due to blood flow and the presence of papillary muscles with signal intensities similar to myocardium make it harder to delineate the endocardial wall. Tissues surrounding the epicardium (fat, lung), which have different intensity profiles and show poor contrast with the myocardium, make the segmentation of the epicardial difficult. Segmentation complexity also depends on the slice level of the image. Apical and basal slice images are more difficult to segment than mid-ventricular images. Indeed, MRI resolution is not high enough to resolve the size of small structures at the apex and ventricle shapes are strongly modified close to the base of the heart, because of the vicinity of the atria [1]. Also, MRI data suffers from inherent noise due to the bias in magnetic field. Dynamic motion of heart causes inhomogeneity of intensity and high variations in contrasts. An irregular crescent shape of the right ventricle makes it much harder to segment in comparison with the left ventricle. Moreover, data from the known HCM population has a much higher variability in the shape and size of the heart chambers because of the randomness of hypertrophy in comparison with normal and other pathologies. In this regard, FIG. 3 shows basal, mid ventricular and apical slices from HCM hearts (a, b) and a normal heart (c). The myocardial hypertrophy is pointed to by white arrows. It can be observed that in a normal heart the wall thickness is consistent throughout the LV, whereas in HCM hearts the consistency highly varies.

In deciphering the biomarkers noted above to diagnose heart irregularities pointing to HCM, this disclosure refers to both Cine CMR images (referred to as cine images) and T1 images, both discussed below. The procedures also use standard reference images from available HCM Registries [24] to train, test, and augment MRI data collection in accordance with standards in the industry.

Cine images are short movies that are able to show heart motion throughout the cardiac cycle, in short-axis. Measurement of left ventricular (LV) mass, ejection fraction, percentage of LV mass subtended by scar, and extracellular volume is critical to identification of HCM patients at highest risk. Information from cine images can be very helpful in efficient quantification of such bio markers. To achieve accurate measurements of these variables, segmentation of heart chambers and myocardium regions is required on CMR images.

Figure 4:
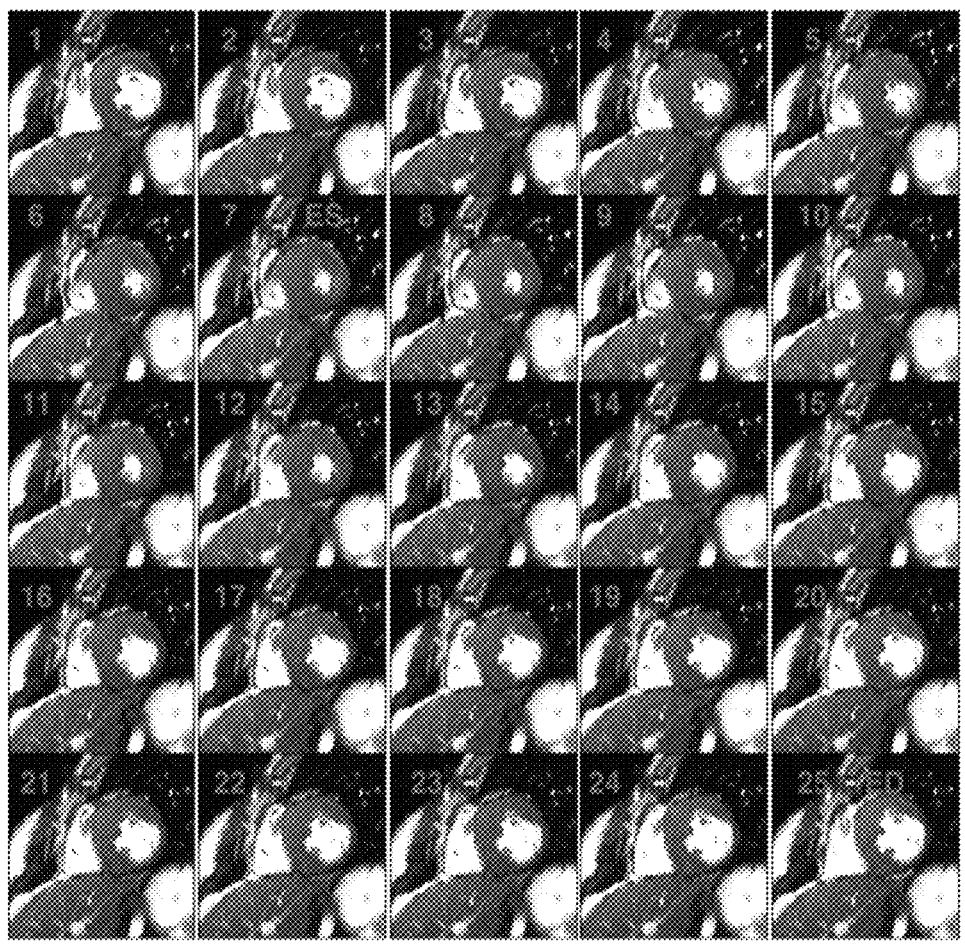
FIG. 4 illustrates a series view of cine image data with twenty-five cardiac phases/frames in sequence on a mid-cavity slice, in which phase 7 is end-systole and end phase 25 is end-diastole imagery.

Cine images are obtained with electrocardiogram (ECG) triggered segmented imaging. Segmented acquisition is the process of dividing the cardiac cycle into multiple segments to produce a series of images that can be displayed as a movie. The cardiac cycle begins with an R wave of the electrocardiogram, ends with the subsequent R wave and is typically divided into 10 to 20 segments, depending on the heart rate. Without limiting this disclosure to any single example, each image in the cine is typically composed of information gathered over several heart beats allowing for a movie to be acquired with a breath hold of 10 to 20 seconds, depending on the sequence. As in any movie, the final cine is a sequence of individual frames. These images can be very helpful in studying cardiac function, valvular function, and movement of blood through the heart. In the cardiac cycle, which is comprised of multiple phases represented by different frames in the cine, this disclosure examines two phases, namely end-diastole and end-systole. At end-diastole, the myocardium is completely relaxed and is fully filled with blood that will be pumped in the following systole phase. At end-systole, the myocardium is completely contracted and has pumped all the blood it can, out of the ventricle. To illustrate the usefulness if cine image data, FIG. 4 shows the cine on one slice, the cine includes end-systole and end-diastole which are marked correspondingly.

Figure 5:
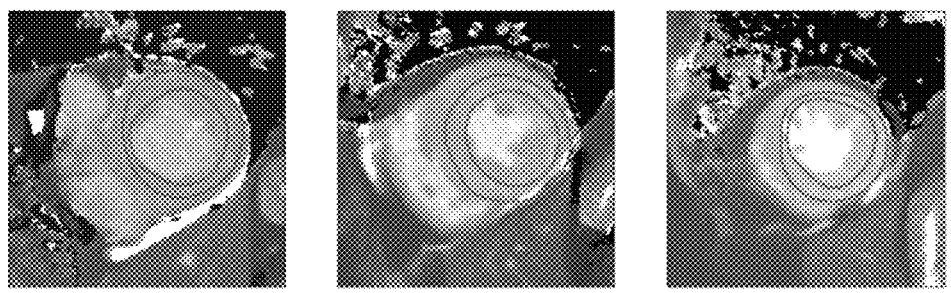
FIG. 5 illustrates a series of native T1 maps at basal, mid-sequence and apical slices in order from left to right.

In other embodiments disclosed herein, processes for MRI diagnostic purposes use T1 data as an output from the imaging procedures. Embodiments of this disclosure illustrate the use of native T1 maps to segment out the left ventricle (LV). The LV epicardial and endocardial ground truth contours are available from known HCM Registry data for all corresponding images. Data preprocessing is fairly similar to that of cine data. As T1 maps are only acquired at basal, mid-cavity and apical positions rather than on all slices that cover the entire heart, the procedures herein use 2D versions of data augmentations to warp each 2D image. To illustrate basic T1 data, FIG. 5 illustrates native T1 maps at basal, mid-sequence and apical slices along with the epi and endocardial (red and green respectively) contours.

Beginning with cine data segmentation, a single model is used to segment both the LV and RV epicardium with three labels of output: background, LV chamber and RV chamber. During training of the convolutional protocol, random 3D affine transformation including translation, rotation, scaling and shear was used on the fly to augment the dataset. Adam optimizer is used with a learning rate of 5e-4 to minimize the loss. The model was trained for 800 epochs on a TitanX GPU for 8 hrs. For both LV and RV, only one fully connected component is retained during post-processing.

Endocardium Segmentation—Diastole

As the endocardium is always inside the epicardium, to maximize the efficiency of the network by focusing on the myocardium-blood contrast, two separate image models are trained for LV and RV endocardial segmentation on masked images. Afterward, the segmentation task is a pixel-wise binary classification problem.

During training, ground truth epicardium masks are used to obtain a tight bounding box that encloses the contour. The images are then cropped accordingly and pixels outside the epicardium are also masked out. As a comparison, the protocols used herein also trained models without images to check their contribution to the performance. The cropped images are then resized to 128×128×32 dimensions to ensure that all inputs to the model have the same size. Similar affine augmentations is performed as well. During testing, results from the corresponding epicardium segmentation generated by the model are used for masking and bounding box extraction.

Adam optimizer was used with a learning rate of 5e-4 to minimize the loss on both models which were trained for 400 epochs on a TitanX GPU for 4 hrs each.

Endocardium Segmentation—Systole

Although training augmentation of the images at end-diastole phase can mimic end-systole images for general cardiac MRI, results discussed below show that the model trained with end-diastole images performs poorly on end-systole images for HCM patients since the shape and contrast is drastically different between the two phases. In some extreme cases where wall thickening is severe, no blood signal is visible, yet the chamber boundary still should be drawn. As ground truth epicardium masks are not available at systole, the cascaded approach is often unavailable. Individual models were then used for the endo segmentation of LV and RV on the original images. Adam optimizer was used with a learning rate of 5e-4 to minimize the loss on both models which were trained for 200 epochs on a Titan X GPU for 4 hours in total.

T1 Segmentation

Segmentation of T1 maps is fairly straight forward and highly similar to the strategy followed for systole endocardium. Training two different models with the computerized methods of this disclosures provides one model to segment LV epicardium and the other model to segment LV endocardium. While segmenting the endocardium, the results below proceeded from masking the input image with the results of epicardium segmentation. Adam optimizer was used with a learning rate of 5e-4 to minimize the loss on both models which were trained for 200 epochs on a Titan X GPU for 4 hours in total.

Biomarker Quantification

In addition to ejection fraction and LV, RV mass, abnormal wall thickening is one characteristic of HCM. Therefore, regional wall thickness on different myocardium segments needs to be calculated for further analysis.

Wall Thickness

Figure 8:
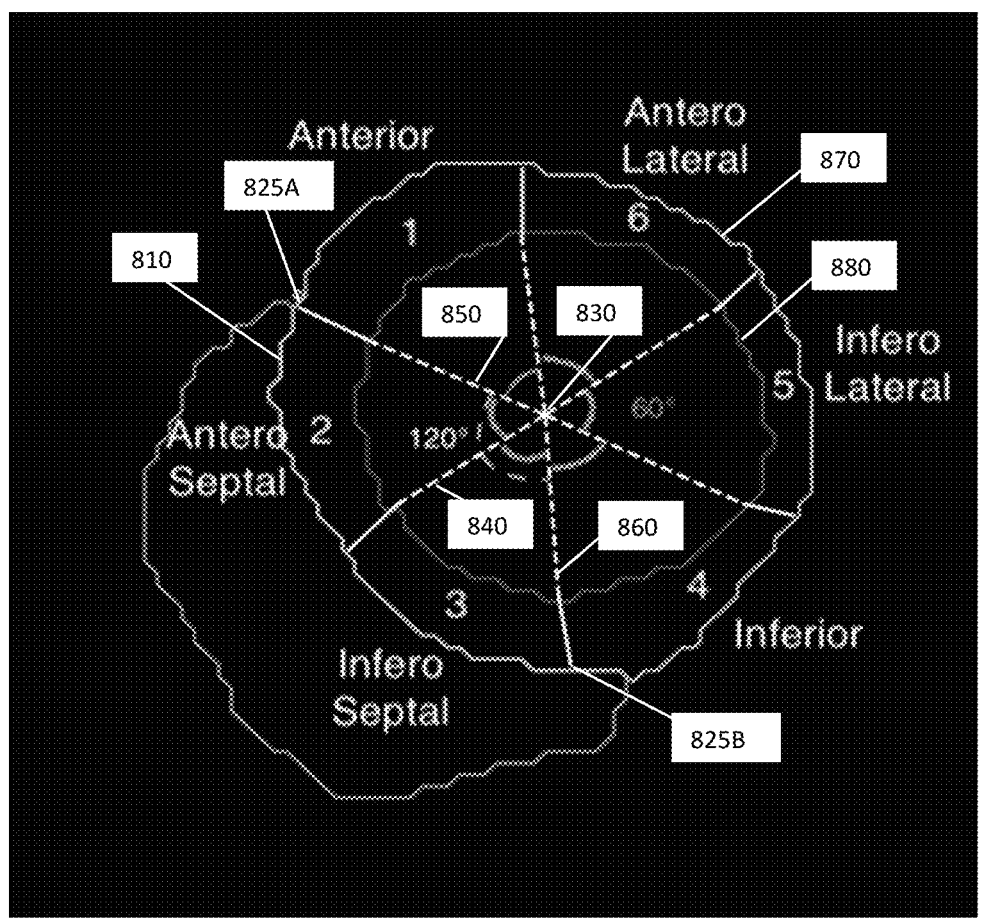
FIG. 8 is a geometric representation of a method for division of a left ventricle of a subject's heart into six equal segments—anterior, antero septal, infero septal, inferior, infero lateral, antero lateral according to the methods disclosed herein.

Wall thickness calculations are made by using all slices, including apical, and dividing the same into 6 segments. FIG. 8 shows the division of left ventricle into six segments of 60° each on a mid-ventricular slice. Segments 2 and 3 are first found by identifying the septum, which is the overlap of LV and RV epi contours. The exact boundaries of the two segments are symmetrically adjusted to make sure the angle is 120°. Segments 1, 6, 5, 4 can be found by dividing the remaining area into four equal parts. Myocardium thickness is calculated at the beginning of each segment—represented by solid white lines in FIG. 8. The same angles are used for all other slices for myocardium division.

Ejection Fraction, LV & RV Mass

Simpson's rule is used to calculate endocardial volumes at end-diastole (EDV) and end-systole (ESV). Ejection fraction (EF) can be found by the below formula. EFs of both LV and RV are calculated.

$$EF = \frac{EDV - ESV}{EDV} * 100$$

Mass calculations require epicardial volumes in addition to endocardial volumes. As epi contours are not available at end-systole, mass is only calculated at end-diastole. Myocardial volume is calculated as the difference of epi and endocardial volumes. Mass is calculated as the product of myocardial volume and density, which was assumed to be constant at 1.05 g/cc.

Mean Myocardial T1

Changes in myocardial T1 can be a very helpful biomarker in identifying risk associated with HCM. It is calculated by taking the average of all the pixel values that lie in the myocardium, which is identified from the corresponding segmentation masks on T1 maps.

One non-limiting goal of this work is to automate the rapid and robust quantification of biomarkers including left and right ventricular mass, ejection fraction and myocardial wall thickness, from cine images, and mean myocardial T1 from native T1 maps for identification of HCM patients at risk. To achieve accurate measurements of these variables, segmentation of heart chambers and myocardium regions is required on cine images across all short-axis slices and for at least end-diastole and end-systole phases, and on native T1 maps. Currently the segmentation is performed manually by experienced cardiologists, so it is time-consuming and suffers from inter-observer variability with reduced biomarker quantification accuracy and robustness, especially in a multi-site study. Automating the biomarker quantification involves an automatic heart chamber segmentation task.

Existing automatic cardiac MRI segmentation techniques can broadly be classified into two groups—ones that need no prior information [2-7] and ones that need weak or strong prior knowledge [8-10]. The former includes techniques that are primarily image-driven which use the pixel intensity differences to distinguish between different regions of interest. The latter techniques are often model-driven, using statistical information extracted from manually annotated training data that describe the spatial relationships of the LV and RV objects and their surrounding structures, knowledge of the heart biomechanics, or anatomical assumptions about the statistical shapes of the objects. Such assumptions about the objects, through either weak or strong priors, contributes to the propensity of these methods to overfit on a particular training dataset, thus making them less generalizable.

Among the approaches that need no prior information, which includes active contours or snakes techniques, pixel classification using clustering algorithms, region growing algorithms, and learning based techniques, accurate fully automatic segmentation is only achievable using learning based techniques. These include techniques based on random forests [11-13], markov random fields [5-14] (MRF), conditional random fields [15, 16] (CRF), restricted boltzman machines [17] (RBM) and deep learning. Methods using random forests rely on image intensity and define the segmentation problem as a classification task. These methods have multiple stages of intensity standardization, estimation and normalization, which are computationally expensive and affect the success of further steps. Moreover, their performance is rather mediocre at basal and apical slices and overall inferior to the state-of-the-art. MRFs and RBMs try to learn the probability of input data. Computing the image probability and parameter estimation in generative models is generally difficult and can lead to reduced performance if oversimplified. Besides, they use the Gibbs sampling algorithm for training, which can be slow, become stuck for correlated inputs, and produce different results each time it is run due to its randomized nature. Alternatively, CRF methods try to model the conditional probability of latent variables, instead of the input data. However, they are still computationally difficult, due to complexity of parameter estimation, and their convergence is not guaranteed. Deep learning techniques, that received much attention over the course of last 5 years, are much more stable and achieve a better performance in comparison with the techniques mentioned earlier.

Processes discussed herein take advantage of image analysis by use of convolutional neural networks (CNNs). CNNs are multi-layer feed-forward networks specifically designed to recognize features in image data. A typical application of CNNs consists of recognition of various objects in images. However convolutional networks have been successfully used for various different tasks, too. The neurons in CNNs work by considering a small portion of the image, referred to herein as a patch. The patches are inspected for features that can be recognized by the network. As a simple example, a feature may be a vertical line, an arch, or a circle. These features are then captured by the respective feature maps of the network. A combination of features is then used to classify the image, or in our case, each pixel.

Deep convolutional neural networks (DCNN) have shown great promise in many medical image segmentation tasks, including cardiac MRI. A majority of these only focus on segmenting the LV for ejection fraction calculation. Yang et al. [18] proposed a fully convolutional architecture to segment the LV myocardium which is relatively shallow, consisting of three convolutional blocks with two of them followed by max pooling and one 4 stride deconvolution to regain the original image dimension. An average of dice score of 0.75 was reported on the CMR dataset from York University, Avendi et al. [19], proposed a hybrid approach that uses deformable models in conjunction with deep learning. A fully convolutional network is used to locate the LV, a stacked auto encoder is then used to infer the shape of the ventricle which is then used by a deformable model to accurately segment the region of interest. The main limitation of this method is that it is multi-stage and requires manual offline training along with extensive hyper-parameter tuning, which can be cumbersome and difficult to generalize to multi-site data. Tran et al. [20] proposed a 15-layered architecture that uses 2D data, which achieved the state-of-art dice scores of 0.96 on epicardium and 0.92 on endocardium using the Sunnybrook dataset. Despite being the state-of-art, this technique uses 2D data, ignoring the overall shape of the LV which could be crucial in identifying the edge slices that shouldn't be segmented.

Although efficient, using the simple convolutional operation might not yield the best feature extraction at times when the regions of interest have complex shapes. Moreover, using larger kernels to increase the effective receptive field (the dimension of the original image viewed by a convolutional layer) size so as to infer more spatial information is not always efficient as there will be a lot more parameters to train which not only takes longer, but could also lead to overfitting. To overcome these issues, this disclosure includes incorporating dilated convolutions into the appropriate CNN.

Dilated Convolution

In general, the receptive field of the CNN should be larger the region of interest being segmented so as to acquire enough spatial information. A simple way of increasing the receptive field is to use a larger convolutional kernel. But doing so also increases the number of parameters that are to be trained which not only increases the time to convergence of the gradient descent algorithm but also increases the chance of overfitting on the training data. To overcome this issue the idea of dilated convolutions [22] was put forth. In simple terms, dilated convolution is a convolution applied to input with defined gaps. With this definition, given our input is an 2D image, dilation rate k=1 is normal convolution and k=2 means skipping one pixel per input and k=4 means skipping 3 pixels.

The training phase of a CNN involves calculation of the loss term and back propagation of the loss through the entire network. The loss term represents the error in prediction made by the CNN on an input. The gradients computed on each layer represent the contribution of that layer to the final loss term. When back propagating, all the trainable parameters are updated according to their gradients. When this is repeated on all training inputs for several epochs, the parameters will be updated in a way that they approximate a non-linear function that models the task at hand.

Segmentation Using CNNs

Image segmentation using CNNs is a classification task on a pixel level. Fully Convolutional Networks (FCN) (CNNs with all convolutional layers) popularized CNN architectures for dense predictions. This allowed segmentation maps to be generated for image of any size. Almost all the subsequent state of the art approaches on segmentation adopted this paradigm. One of the main problems with using CNNs for segmentation is pooling layers. Pooling layers increase the field of view and are able to aggregate the context while discarding the 'where' information. However, segmentation requires the exact alignment of class maps and therefore, needs the 'where' information to be preserved. Encoder-Decoder style network architecture was proposed to tackle this issue. Encoder gradually reduces the spatial dimension with pooling layers and decoder gradually recovers the object details and spatial dimension. There are usually shortcut connections from encoder to decoder to help decoder recover the object details better.

3D UNet

Figure 6:
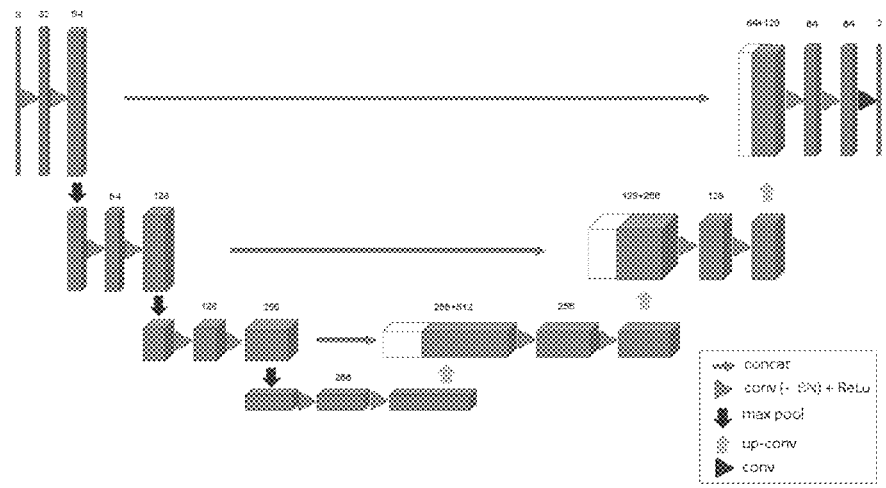
FIG. 6 is a PRIOR ART representation of a 3D u-net architecture for convolutional neural networks, as disclosed in Reference [26] cited below.
Figure 7:
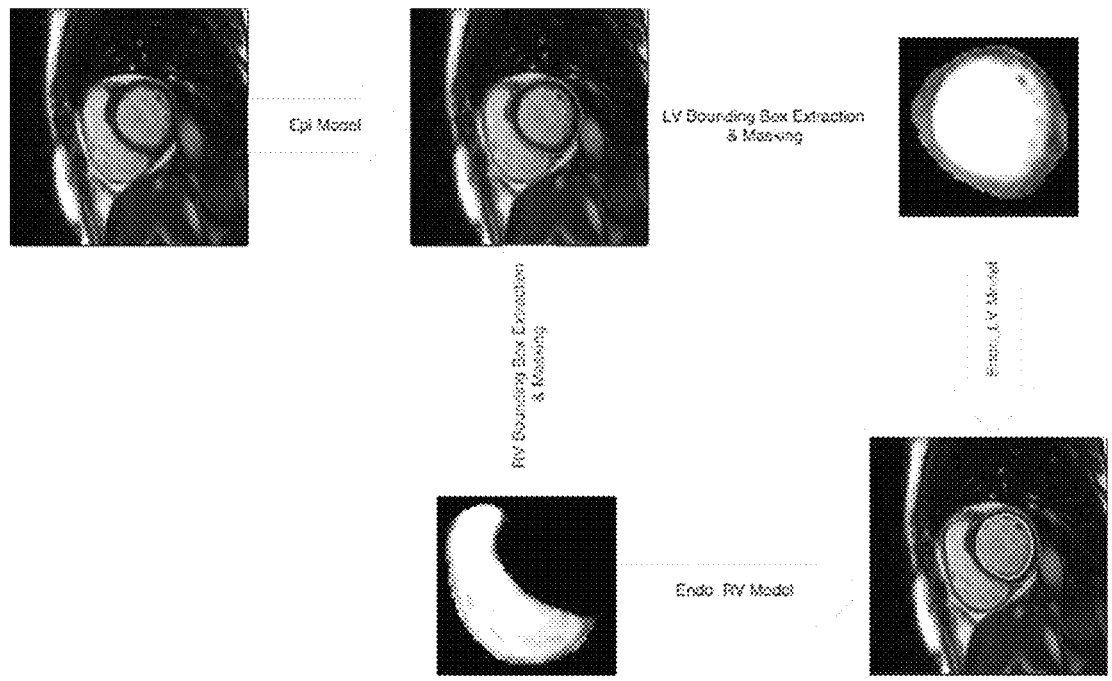
FIG. 7 is a schematic representation of workflow of the cascaded DCNN approach for end-diastole cardiac chamber as disclosed herein.

3D UNet was originally proposed by Cicek et al. [23] for automatic segmentation of *Xenopus* (a highly aquatic frog) kidney. It has an encoder-decoder style architecture with skip connections between corresponding layers in encoding and decoding paths. This architecture is very popular for medical image segmentation. All the deep learning models used in this study have the same architecture, the 3D UNet. 3D in the name indicates that the input to this network is a 3D image. UNet refers to the structure of the network, which resembles the letter 'U'. FIG. 6 shows the block representation of 3D UNet architecture.

Each convolutional block has two convolutions followed by max pooling. Every convolution is immediately followed by a rectified linear unit (ReLU) activation and batch normalization layer. Each deconvolutional block consists of two convolutions followed by a deconvolution to regain spatial dimension. Moreover, there are skip connections from the encoding path to decoding path at corresponding spatial dimensions. These are shown by green arrows. The very final convolution (shown by a purple arrow) that generates a three-dimensional feature map is followed by a softmax activation in order to obtain a pseudo-random probability distribution at each pixel representing its class membership. All the deep learning models used in this work have the UNet architecture A segmenting procedure according to this disclosure is adapted to HCM diagnosis, in part by the workflow shown in FIG. 7 of the attached drawings. A cascaded deep learning based approach was developed to accurately segment the heart chambers and thereby automate the quantification of HCM biomarkers. First, accurate segmentations for LV and RV epicardium are obtained with one network. Results from the epi segmentation are then used to obtain tight bounding boxes that encloses the LV and RV chamber, respectively. Separate models are trained for endocardium segmentation for each chamber. Input images are also masked by the results from epi segmentation so that the network can focus on the inside of the chamber. The following sub sections further discuss each step of the workflow shown in FIG. 7.

DCNN Architecture and Loss Metric

A 3D-UNet style architecture is used for the segmentation in both steps. Convolutions in the encoding phase of 3D-UNet were replaced with dilated convolutions to increase the receptive field without having to train more parameters. In medical images, the ground truth masks are dominated by background leading to an overwhelming class imbalance, especially when there are multiple foreground classes.

This can be addressed by applying a weight map to the categorical-cross entropy loss function or by using a dice-similarity metric-based loss function [13]. The latter is usually preferred as it does not rely on hyper parameters. With multiple foreground labels, the loss is given as:

$$\text{Loss} = 1 - \frac{\sum_{i=1}^{n} \text{Dice}_i}{n}$$

where n is the number of classes, excluding background and each individual dice is calculated using Sorenson's coefficient.

Evaluation

Dice scores and average perpendicular distance (APD) are calculated to evaluate the segmentation quality. To demonstrate the necessity of different models for HCM patients, the procedure also trained a model for LV epicardium and endocardium segmentation using the SunnyBrook dataset, which contains normal and other patient populations, and tested the model on HCM patients.

Dice Score

The dice score is a statistic used for comparing the similarity of two samples. When applied to boolean data, using the definition of true positive (TP), false positive (FP), and false negative (FN), it can be written as:

$$DSC = \frac{2TP}{2TP + FP + FN}.$$

The value of dice score ranges from 0 to 1 with 0 being complete mismatch and 1 being perfect overlay.

Average Perpendicular Distance

The average perpendicular distance (APD) measures the distance from the automatically segmented contour to the corresponding manually drawn expert contour, averaged over all contour points. A high value implies that the two contours do not match closely. In general, and APD value less than 5 mm is considered a good contour. Considering a pixel spacing of 1 mm, the APD for the above example is 1.426 mm, maximum distance is 5.45 mm and minimum distance is 0 mm.

Symmetric Mean Absolute Percentage Error

Symmetric mean absolute percentage error (sMAPE) is an accuracy measure based on percentage (or relative) errors. It is used to evaluate the quantification of biomarkers. For a set of actual values A and predicted values P, sMAPE is given by $$sMAPE = \frac{100\%}{n} \sum_{t=1}^{n} \frac{|P_t - A_t|}{(|P_t| + |A_t|)}$$

within the meaning and range of equivalents thereof are intended to be embraced therein.

Results

Figure 9:
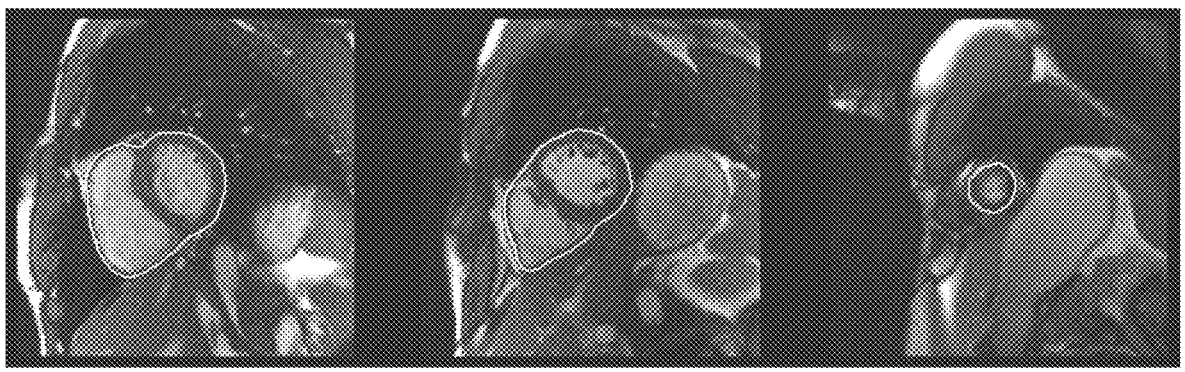
FIG. 9 illustrates MRI images subject to segmenting according to the disclosure herein for a) left ventricle (LV) and right ventricle (RV) Epicardium, b) right ventricle (RV) Endocardium, and c) left ventricle (LV) endocardium where ground truth contour is show in blue and use of the model output, according to the disclosure below, is set forth in yellow.
Figure 9:
Figure 9:

Results for segmentation of epicardium and endocardium of both LV and RV are shown in FIG. 9 with ground truth contours in blue and the model output in yellow. FIG. 9a shows the combined LV and RV epicardium, 9b the RV endocardium and 9c the LV endocardium. Alongside this, the average dice scores for these ROIs is reported in Table 1 set forth herein.

TABLE 1

Average DICE scores

| Combined LV, RV Epi | Endo-LV | Endo-RV |
|---|---|---|
| 0.8991 | 0.8788 | 0.7621 |

Figure 10:
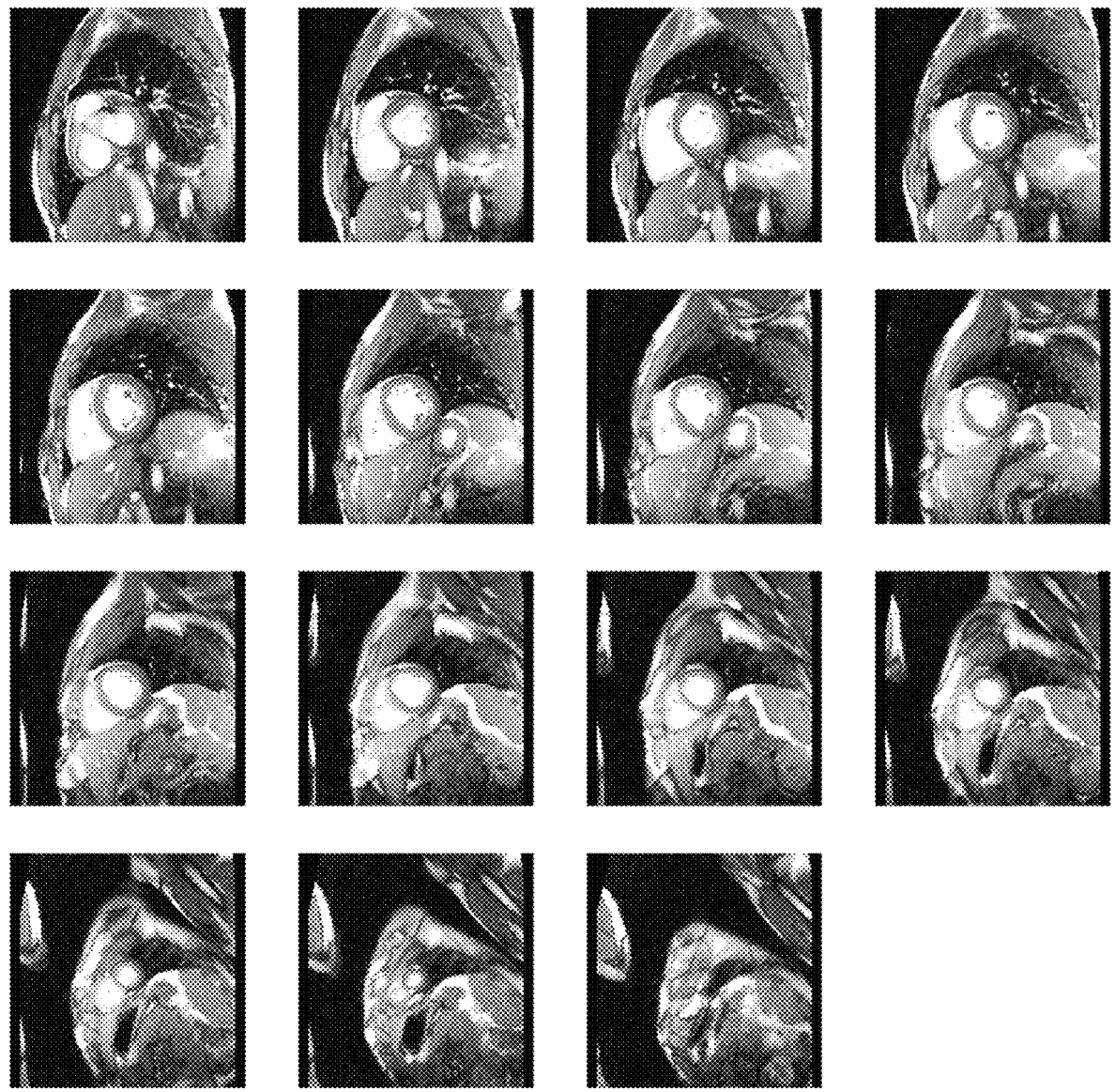
FIG. 10 illustrates a series of MRI images with automatic segmentation results on cine data images for one patient at end-diastole according to the disclosure herein.

The following material illustrates a brief review of the steps described in this disclosure to achieve the results discussed herein:

In a first dataset of cine image data, the procedure included selecting 69 patients from a single institution with manually drawn and verified segmentation for epicardial and endocardial contours of LV and RV. The coverage was 10-15 short-axis slices with 8 mm slice thickness covering entire LV and RV. The imaging biomarkers retrieved were LV and RV mass, ejection fraction and wall thickness at different segments. FIG. 10 shows the automatic segmentation results for one patient at end diastole.

Figure 11:
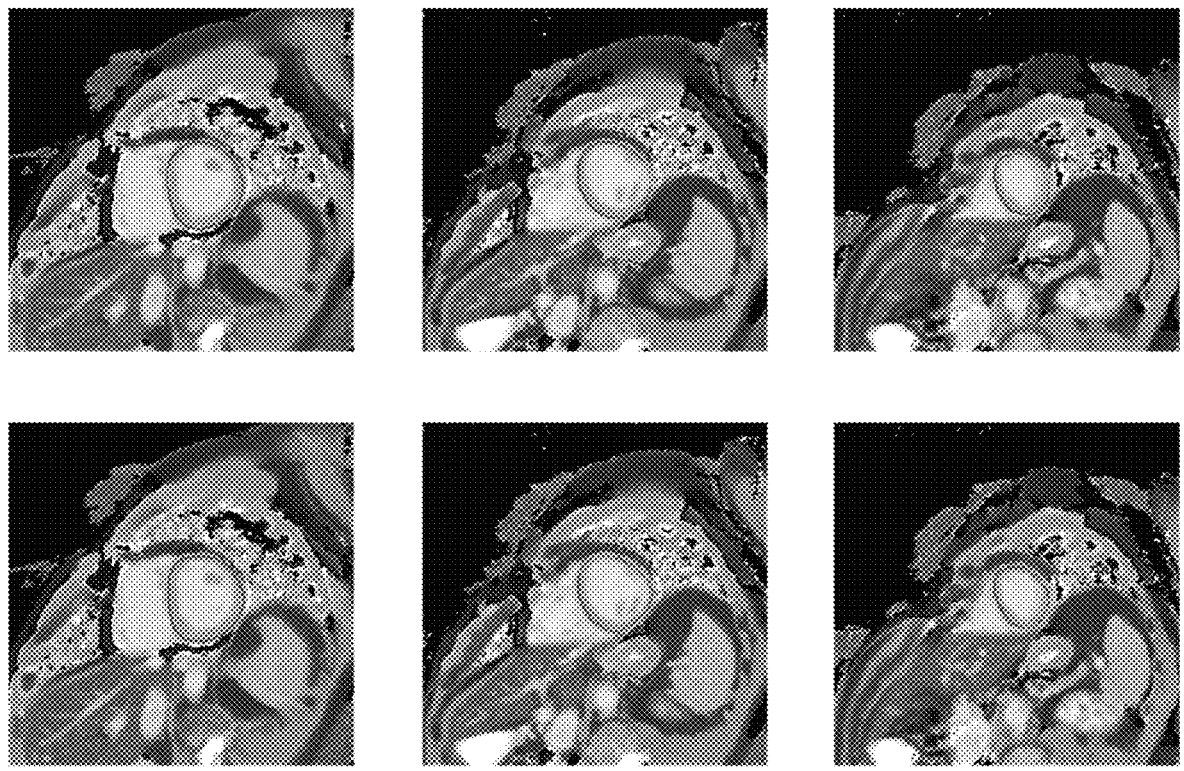
FIG. 11 illustrates a series of MRI images with automatic (top) and manual (bottom) segmentation on T1 maps.

In a second dataset of T1 image data, the procedure included selected 67 patients from two institutions with verified segmentation for epicardial and endocardial contours of LV with 1-4 T1 maps (pre-contrast, 5 min, 14 min, 29 min post-contrast). The coverage included 3 short-axis slices at apex, mid-ventricle, and base. The resulting imaging biomarker was a mean T1 value. FIG. 11 shows the automatic (top) and manual (bottom) segmentation on T1 maps.

Figure 12:
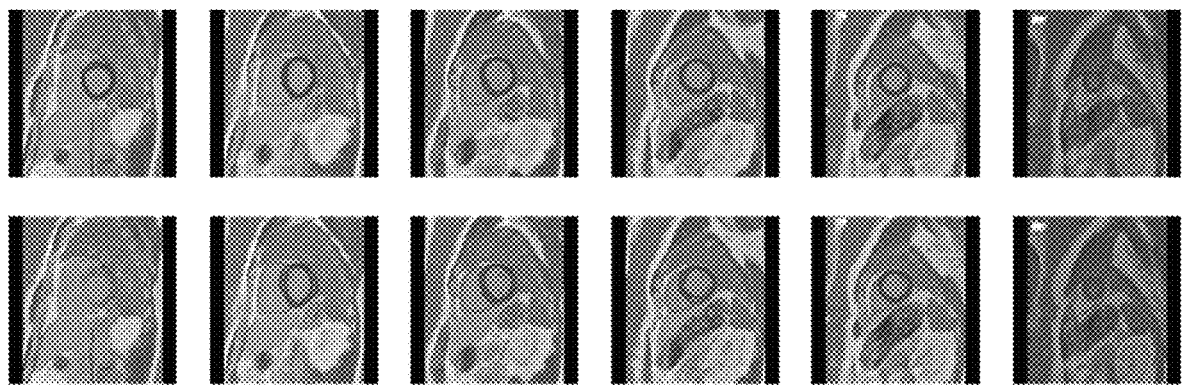
FIG. 12 illustrates a series of MRI images with automatic (top) and manual (bottom) segmentation on LGE images.

In a third dataset that included images with Late Gadolinium Enhancement (LGE), the procedure included selecting 63 patients from a single institution with verified epicardium and endocardium contours of LV. [27]. FIG. 12 shows the automatic (top) and manual (bottom) segmentation on LGE.

The segmentation of the above noted data sets included a deep convolutional neural network structure (DCNN) with a 2-dimensional U-Net having dilated convolutions to increase the receptive field without introducing more parameters. The workflow generally included, but is not limited to, pre-processing by unifying the spatial resolution and matrix size. For cine data, the procedures utilized separate networks to train epicardial (LV and RV) and endocardial contours. One should note that use of a DCNN included training augmentation, such as but not limited to, random b-spline based deformation and affine transformation. Testing augmentation included, but is not limited to, rotating the input images and averaging the output. Post-processing steps included, but are not limited to, removing isolated regions and combining the results from epicardial and endocardial contours.

Results of the segmenting analysis allows for biomarker extraction for diagnostic purposes. Upon calculating LV and RV volume, mass, and ejection fraction, the procedure continues by summing up all the relevant pixels and multiplying by the voxel size (partial volume effect is ignored) to calculate the volume before calculating the corresponding mass or ejection fraction variable. In certain embodiments, the results described herein are achieved by using a first set of cascaded convolutional neural networks (CNN) operating with cine image data sets to segment respective portions of the plurality of images corresponding to respective epicardium layers and endocardium layers for a left ventricle (LV) and a right ventricle (RV) of the heart and using a second set of cascaded convolutional neural networks (CNN) operating on T1 image data sets to segment additional images corresponding to the respective epicardium layer and endocardium layer for the LV of the heart.

Along those lines, the method includes using the first set of cascaded convolutional neural networks (CNN) to segment cine image data sets by (i) applying a first cine data CNN to first selected image data representing the LV and the RV epicardium portions of the heart; (ii) applying a second cine data CNN to second selected image data representing the LV endocardium portion of the heart; and (iii) applying a third cine data CNN to third selected image data representing the RV endocardium portion of the heart.

Using the second set of cascaded convolutional neural networks (CNN) to segment T1 image data may include (i) applying a first T1 data CNN to fourth selected image data representing the LV epicardium portion of the heart; and (ii)

applying a second T1 data CNN to fifth selected image data representing the LV endocardium portion of the heart.

As noted briefly above, one of the goals of this disclosure is to accurately determine LV wall thickness for HCM diagnosis. FIG. 8 of the attached drawings shows one non-limiting embodiment of calculating wall thickness by automatically dividing the myocardium into six segments (1-6). Next, the cine image data is subject to the steps of this disclosure, that identify the two RV insertion points, by obtaining the intersection area (810) of LV and RV epicardial contours and getting the boundary points (825A, 825B). The image data is then analyzed with the above noted CNN to find the center of mass (830) of the LV. In a geometrical operation, the image data is manipulated to identify a bisector line (840) of two additional lines (850, 860) connecting the LV center of mass (830) to the two insertion points, respectively. Finally, the method of this disclosure rotates the bisector by 60°, 120°, 180°, 240°, 300° to get all 6 lines and calculate their intersections to the LV epicardium (870) and endocardium (880) contours.

Using the above noted quality and accuracy calculations on the data shows that the cine segmentation exhibits the following for quality and accuracy as shown in Table 2:

TABLE 2

Dice and MSD for different regions and different phases
(ED: end-diastole, ES: end-systole) on cine images

|  | Dice | MSD (mm) |
|---|---|---|
| LV epi-ED | 0.939 ± 0.028 | 2.234 +/− 1.630 |
| LV-endo-ED | 0.937 ± 0.024 | 1.708 +/− 1.239 |
| RV-epi-ED | 0.861 ± 0.041 | 2.609 +/− 0.957 |
| RV-endo-ED | 0.859 ± 0.043 | 2.579 +/− 1.228 |
| LV-endo-ES | 0.822 ± 0.071 | 2.469 +/− 1.525 |
| RV-endo-ES | 0.750 ± 0.127 | 3.152 +/− 1.911 |

T1 & LGE segmentation quality and accuracy are summarized in Table 3:

TABLE 3

Dice scores for epi and endo contours
on T1 maps and LGE images

|  | Dice |
|---|---|
| T1-epi | 0.938 +/− 0.036 |
| T1-endo | 0.916 +/− 0.046 |
| LGE-epi | 0.926 +/− 0.044 |
| LGE-endo | 0./920 +/− 0.041 |

Biomarker quantification quality and accuracy:

TABLE 4

Mean absolute percentage error
(MAPE) of imaging biomarkers

|  | MAPE (%) |
|---|---|
| LV-mass | 11.41 +/− 8.64 |
| LV-EF | 9.49 +/− 7.41 |
| RV-mass | 26.95 +/− 25.61 |
| RV-EF | 11.35 +/− 10.56 |
| LV-mean thickness | 18.06 +/− 7.68 |
| LV-mean T1 | 1.55 +/− 1.85 |

This disclosure utilizes, in part the following validation protocol steps by randomly splitting the image dataset using a 3:2 ratio for training and validation on the patient level.

The Dice score is calculated over the whole image stack, and mean surface distance (MSD) is calculated over each slice. To complete biomarker quantification, the protocol of this disclosure includes, but is not limited to, using the same extraction method on the ground-truth contours and the automatically segmented contours. Mean absolute percentage error (MAPE) is then calculated for the biomarkers across a set "n" of actual biomarker values versus the corresponding forecast values provided by the automated procedures as follows:

$$M = \frac{100\%}{n} \sum_{t=1}^{n} \left| \frac{A_t - F_t}{A_t} \right|,$$

Table 5 summarizes the results of biomarker quantification. For comparison, root mean square error (RMSE) values from model predictions and an inter-observer study on generic cardiac MRI data are reported [15]. Wall thickness measurements are only done at end-diastole as no epicarcial contours are available for end-systole. The inter observer RMSE values reported in Table 5 are from a population that is representative of healthy patients. [25]

TABLE 5

Quantification results for LV, RV Mass, Ejection Fraction,
Mean myocardial T1 and the End-Diastole wall thickness.

| Biomarker | sMAPE in % | Model_RMSE | InterObserver_ RMSE (Generic Cardiac MRI) |
|---|---|---|---|
| LV Mass | 13.7 ± 8.9 | 52.4 gm | 17.5 gm |
| RV Mass | 32.2 ± 18.9 | 16.4 gm | N/A |
| LV Ejection Fraction | 5.8 ± 4.5 | 9.5% | 4.2% |
| RV Ejection Fraction | 9.2 ± 5.9 | 21.6% | N/A |
| Wall Thickness | 20.8 ± 8.1 | 2.97 mm | N/A |
| Mean Myocardial T1 | 2.91 ± 2.96 | 54.5 msec | N/A |

RMSE values on HCM population are expected to be higher given the increased variability in the size and shape of heart chambers. Higher errors in RV related values are a result of poor segmentation in comparison with LV. Moreover, the poor performance in basal slice segmentation contributes significantly to the errors in mass and ejection fraction calculations. For myocardial T1, in general the values are around 1000 msecs. RMSE of 54.5 msec and sMAPE of 2.9% indicates a robust quantification.

CONCLUSION

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The patentable scope of certain embodiments of the disclosed technology is indicated by the appended claims, rather than the foregoing description.

REFERENCES

1. Petitjean C, Dacher J-N. A review of segmentation methods in short axis cardiac MR images. *Med Image Anal.* 2011; 15(2):169-184.

2. Kedenburg G, Cocosco C A, Köthe U, Niessen W J, Vonken E P A, Viergever M A. Automatic cardiac MRI myocardium segmentation using graphcut. In: *Medical Imaging 2006: Image Processing*. Vol 6144; 2006: 61440A.
3. Cocosco C A, Niessen W J, Netsch T, et al. Automatic image-driven segmentation of the ventricles in cardiac cine MRI. *J Magn Reson Imaging*. 2008; 28(2):366-374.
4. Jolly M. Fully automatic left ventricle segmentation in cardiac cine MR images using registration and minimum surfaces. *MIDAS Journal-Cardiac MR Left Vent Segmentation Chall*. 2009; 4:59.
5. Huang S, Liu J, Lee L C, et al. An image-based comprehensive approach for automatic segmentation of left ventricle from cardiac short axis cine mr images. *J Digit Imaging*. 2011; 24(4):598-608.
6. Billet F, Sermesant M, Delingette H, Ayache N. Cardiac motion recovery and boundary conditions estimation by coupling an electromechanical model and cine-MRI data. In: *International Conference on Functional Imaging and Modeling of the Heart;* 2009:376-385.
7. Pluempitiwiriyawej C, Moura J M F, Wu Y-J L, Ho C. STACS: New active contour scheme for cardiac MR image segmentation. *IEEE Trans Med Imaging*. 2005; 24(5):593-603.
8. Zhang H, Wahle A, Johnson R K, Scholz T D, Sonka M. 4-D cardiac MR image analysis: left and right ventricular morphology and function. *IEEE Trans Med Imaging*. 2010; 29(2):350-364.
9. Van Assen H C, Danilouchkine M G, Frangi A F, et al. SPASM: a 3D-ASM for segmentation of sparse and arbitrarily oriented cardiac MRI data. *Med Image Anal*. 2006; 10(2):286-303.
10. Zhuang X, Hawkes D J, Crum W R, et al. Robust registration between cardiac MRI images and atlas for segmentation propagation. In: *Medical Imaging 2008: Image Processing*. Vol 6914; 2008:691408.
11. Margeta J, Geremia E, Criminisi A, Ayache N. Layered spatio-temporal forests for left ventricle segmentation from 4D cardiac MRI data. In: *International Workshop on Statistical Atlases and Computational Models of the Heart;* 2011:109-119.
12. Lempitsky V, Verhoek M, Noble J A, Blake A. Random forest classification for automatic delineation of myocardium in real-time 3D echocardiography. In: *International Conference on Functional Imaging and Modeling of the Heart;* 2009:447-456.
13. Geremia E, Clatz O, Menze B H, Konukoglu E, Criminisi A, Ayache N. Spatial decision forests for MS lesion segmentation in multi-channel magnetic resonance images. *Neuroimage*. 2011; 57(2):378-390.
14. Cordero-Grande L, Vegas-Sánchez-Ferrero G, Casaseca-de-la-Higuera P, et al. Unsupervised 4D myocardium segmentation with a Markov Random Field based deformable model. *Med Image Anal*. 2011; 15(3):283-301.
15. Cobzas D, Schmidt M. Increased discrimination in level set methods with embedded conditional random fields. In: *Computer Vision and Pattern Recognition, 2009. CVPR 2009. IEEE Conference On;* 2009:328-335.
16. Dreijer J F, Herbst B M, Du Preez J A. Left ventricular segmentation from MRI datasets with edge modelling conditional random fields. *BMC Med Imaging*. 2013; 13(1):24.
17. Ngo T A, Carneiro G. Fully Automated Non-rigid Segmentation with Distance Regularized Level Set Evolution Initialized and Constrained by Deep-Structured Inference. In: *CVPR;* 2014:3118-3125.
18. Yang X L, Gobeawan L, Yeo S Y, Tang W T, Wu Z Z, Su Y. Automatic segmentation of left ventricular myocardium by deep convolutional and de-convolutional neural networks. In: *Computing in Cardiology Conference (CinC)*, 2016; 2016:81-84.
19. Avendi M R, Kheradvar A, Jafarkhani H. A combined deep-learning and deformable-model approach to fully automatic segmentation of the left ventricle in cardiac MRI. *Med Image Anal*. 2016; 30:108-119.
20. Tran P V. A fully convolutional neural network for cardiac segmentation in short-axis MRI. *arXiv Prepr arXiv160400494*. 2016.
21. Avendi M R, Kheradvar A, Jafarkhani H. Automatic segmentation of the right ventricle from cardiac MRI using a learning-based approach. *Magn Reson Med*. 2017; 78(6):2439-2448.
22. Yu F, Koltun V. Multi-scale context aggregation by dilated convolutions. *arXiv Prepr arXiv151107122*. 2015.
23. Bui T D, Shin J, Moon T. 3d densely convolution networks for volumetric segmentation. *arXiv Prepr arXiv170903199*. 2017.
24. Kramer C M, Appelbaum E, Desai M Y, et al. Hypertrophic Cardiomyopathy Registry: The rationale and design of an international, observational study of hypertrophic cardiomyopathy. *Am Heart J*. 2015; 170(2):223-230.
25. Suinesiaputra A, Bluemke D A, Cowan B R, et al. Quantification of LV function and mass by cardiovascular magnetic resonance: multi-center variability and consensus contours. *J Cardiovasc Magn Reson*. 2015; 17(1):63.
26. Çiçek, Özgün et al., 3D U-Net: Learning Dense Volumetric Segmentation from Sparse Annotation published in *MICCAI* 2016.
27. Kramer C M, Appelbaum E, Desai M Y, et al. Hypertrophic Cardiomyopathy Registry (HCMR): The rationale and design of an international, observational study of hypertrophic cardiomyopathy. *Am Heart J*. 2015. 170(2): 223-230.

What is claimed is:

1. A method, comprising:
   acquiring magnetic resonance imaging data, for a plurality of images, of the heart of a subject;
   segmenting, using cascaded convolutional neural networks (CNN), respective portions of the images corresponding to respective epicardium layers and endocardium layers for a left ventricle (LV) and a right ventricle (RV) of the heart;
   extracting biomarker data from segmented portions of the images; and
   assessing hypertrophic cardiomyopathy from the biomarker data.

2. A method according to claim 1, wherein assessing hypertrophic cardiomyopathy comprises extracting biomarker data comprising a LV wall thickness measurement.

3. A method according to claim 1, further comprising segmenting the respective epicardium layers with a first convolutional neural network of the cascaded convolutional neural networks prior to segmenting the endocardium layers.

4. A method according to claim 3, further comprising using segmented epicardium layers to automatically select a region of interest for segmenting the endocardium layers.

5. A method according to claim 4, further comprising segmenting respective endocardium layers for the LV and the RV by respective second and third convolutional neural networks of the cascaded convolutional neural networks on the region of interest.

6. A method according to claim 1, wherein extracting biomarker data comprises calculating a volume quantity for the LV and the RV.

7. A method according to claim 6, further comprising calculating a mass quantity and an ejection fraction for the respective LV and RV from the volume quantity.

8. A method according to claim 1, wherein extracting biomarker data comprises calculating an LV wall thickness by identifying two RV insertion points within the images of the LV by obtaining an intersection area of LV and RV epicardial contours and setting boundary points for the contours within the image data.

9. A method according to claim 8, wherein calculating the LV wall thickness further comprises calculating a position within the image data representing a center of mass of the LV.

10. A method according to claim 9, wherein calculating the LV wall thickness further comprises identifying two respective lines of image data connecting the LV center of mass to the two RV insertion points and identifying at least one bisector line extending between the respective lines of image data and from the LV center of mass toward the intersection area of LV and RV epicardial contours.

11. A method according to claim 10, wherein calculating the LV wall thickness further comprises identifying additional segmenting lines and calculating the LV wall thickness from intersections of the segmenting lines with the epicardium contours and the endocardium contours of the LV.

12. A method according to claim 11, wherein the additional segmenting lines are positioned on the images of the LV wall to define angles with the at least one bisector line, and wherein the angles have increments around the LV wall of about sixty degrees.

13. A method according to claim 1, further comprising standardizing the plurality of images to a selected number of layers and a preset pixel matrix size.

14. A method, comprising:
acquiring magnetic resonance imaging data, for a plurality of images, of the heart of a subject;
using a first set of cascaded convolutional neural networks (CNN) operating with cine image data sets to segment respective portions of the plurality of images corresponding to respective epicardium layers and endocardium layers for a left ventricle (LV) and a right ventricle (RV) of the heart;
using a second set of cascaded convolutional neural networks (CNN) operating on T1 image data sets to segment additional images corresponding to the respective epicardium layer and endocardium layer for the LV of the heart;
extracting biomarker data from segmented portions of the cine image data sets and the T1 image data sets; and
assessing hypertrophic cardiomyopathy from the biomarker data.

15. A method according to claim 14, wherein using the first set of cascaded convolutional neural networks (CNN) to segment cine image data sets further comprises:
(i) applying a first cine data CNN to first selected image data representing the LV and the RV epicardium portions of the heart;
(ii) applying a second cine data CNN to second selected image data representing the LV endocardium portion of the heart; and
(iii) applying a third cine data CNN to third selected image data representing the RV endocardium portion of the heart.

16. A method according to claim 14, wherein using the second set of cascaded convolutional neural networks (CNN) to segment T1 image data comprises:
(i) applying a first T1 data CNN to fourth selected image data representing the LV epicardium portion of the heart; and
(ii) applying a second T1 data CNN to fifth selected image data representing the LV endocardium portion of the heart.

17. A method according to claim 16, further comprising masking the T1 image data of the heart with segmented image data representing the LV epicardium portion of the heart before applying the second T1 data CNN to the LV endocardium portion of the heart.

18. A method according to claim 16, further comprising repeating the second set of cascaded convolutional neural networks (CNN) on the T1 image data after late gadolinium enhancement (LGE).

19. A method according to claim 14, further comprising identifying a myocardium region of the heart from the plurality of images and further identifying changes in myocardial T1 image data by taking an average of respective T1 pixel values representing the myocardium.

20. A method according to claim 14, further comprising applying a dilated convolution into at least one of the first set and the second set of cascaded convolutional networks.

21. A system comprising:
at least one processor;
at least one memory device coupled to the processor and storing computer-readable instructions which, when executed by the at least one processor, cause the system to perform functions that comprise:
acquiring magnetic resonance imaging data, for a plurality of images, of a heart of a subject;
segmenting, using cascaded convolutional neural networks (CNN), respective portions of the images corresponding to respective epicardium layers and endocardium layers for a left ventricle (LV) and a right ventricle (RV) of the heart;
extracting biomarker data from segmented portions of the images; and
assessing hypertrophic cardiomyopathy from the biomarker data.

22. A non-transitory computer-readable medium having stored instructions that, when executed by one or more processors, cause a computing device to perform functions that comprise:
acquiring magnetic resonance imaging data, for a plurality of images, of a heart of a subject;
segmenting, using cascaded convolutional neural networks (CNN), respective portions of the images corresponding to respective epicardium layers and endocardium layers for a left ventricle (LV) and a right ventricle (RV) of the heart;
extracting biomarker data from segmented portions of the images; and
assessing hypertrophic cardiomyopathy from the biomarker data.

* * * * *